United States Patent [19]
Webster, Jr.

[11] Patent Number: 5,411,025
[45] Date of Patent: May 2, 1995

[54] CARDIOVASCULAR CATHETER WITH LATERALLY STABLE BASKET-SHAPED ELECTRODE ARRAY

[75] Inventor: Wilton W. Webster, Jr., Altadena, Calif.

[73] Assignee: Cordis Webster, Inc., Baldwin Park, Calif.

[21] Appl. No.: 906,546

[22] Filed: Jun. 30, 1992

[51] Int. Cl.$^6$ ............................................. A61B 5/0402
[52] U.S. Cl. ...................................... 128/642; 607/122
[58] Field of Search .................... 128/642, 784–786; 607/122, 124

[56] References Cited

U.S. PATENT DOCUMENTS

| | | | |
|---|---|---|---|
| 3,664,347 | 5/1972 | Harmjanz | 128/786 |
| 3,890,977 | 6/1975 | Wilson | 128/785 X |
| 4,522,212 | 6/1985 | Gelmas et al. | 128/642 |
| 4,699,147 | 10/1987 | Chilson et al. | 128/786 X |
| 5,010,894 | 4/1991 | Edhag | 128/785 |
| 5,156,151 | 10/1992 | Imran | 128/642 |

FOREIGN PATENT DOCUMENTS

| | | | |
|---|---|---|---|
| 0009732 | 4/1980 | European Pat. Off. | 128/786 |
| 2659240 | 9/1991 | France | 128/642 |
| 4025369 | 2/1991 | Germany | 128/642 |

Primary Examiner—Lee S. Cohen
Attorney, Agent, or Firm—Christie, Parker & Hale

[57] ABSTRACT

An electrophysiological mapping device includes an outer catheter, an inner catheter slidable within the outer catheter, and an electronic activation and recording device for electrically activating electrodes on the inner catheter and/or recording electric signals received by the electrodes. The distal end of the inner catheter comprises a plurality of arms that carry electrodes. The arms bow outwardly upon extension of the inner catheter from the outer catheter to form a three-dimensional shape. Each arm has a spine of a superelastic material. Each spine is semi-circular in section, and is disposed within a portion of a flexible sheath, the electrode lead wires being disposed in the rest of the sheath. The electrodes are formed from the ends of the insulated electrode lead wires which pass through the sheath, are wrapped around the sheath and then stripped of their insulation. The proximal and distal ends of the spines are fixed to proximal and distal fittings, each having a polygonal segment having flat sides which engage the flat surfaces of the spines and a clamping ring to secure the spines to the segments.

21 Claims, 4 Drawing Sheets

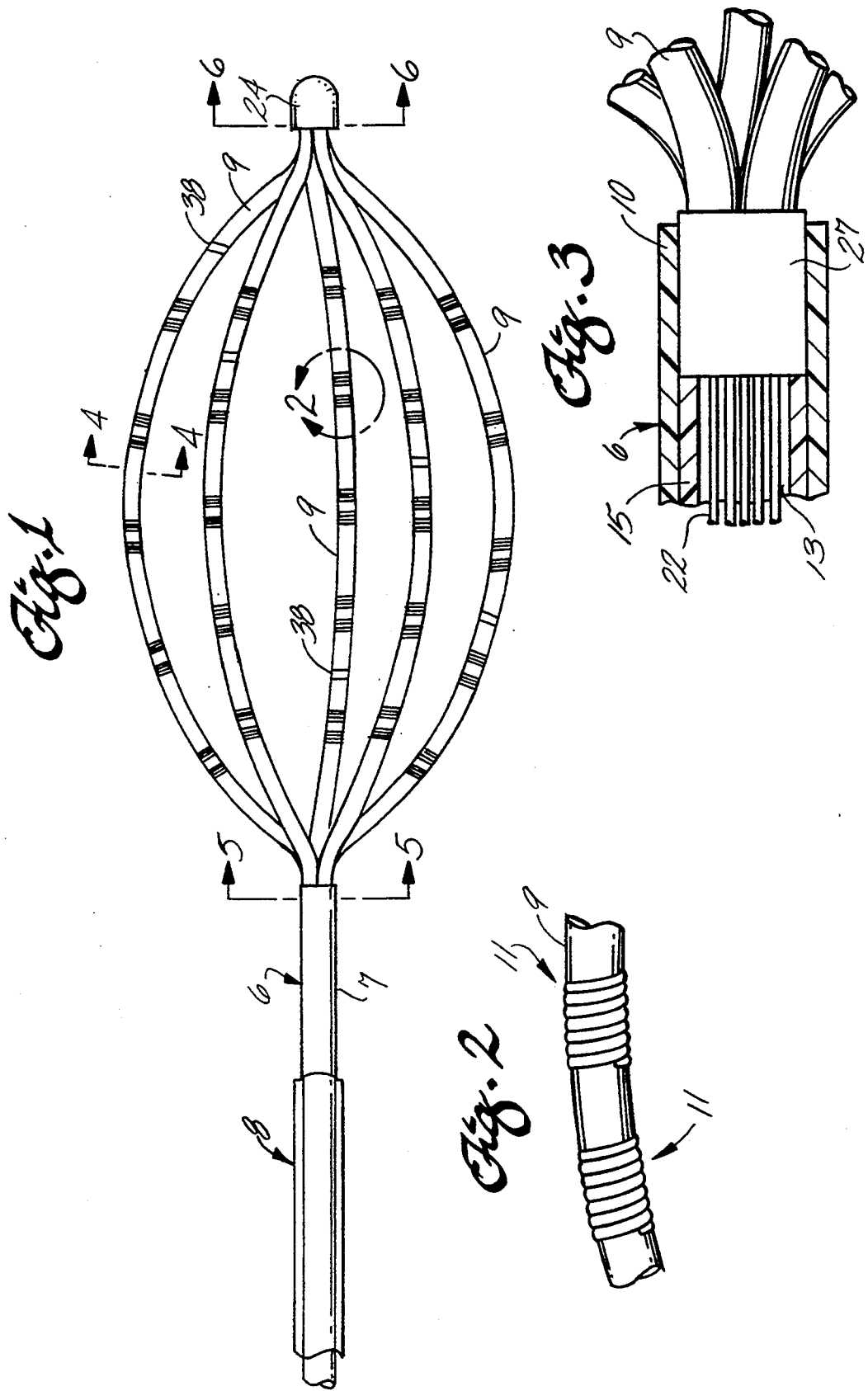

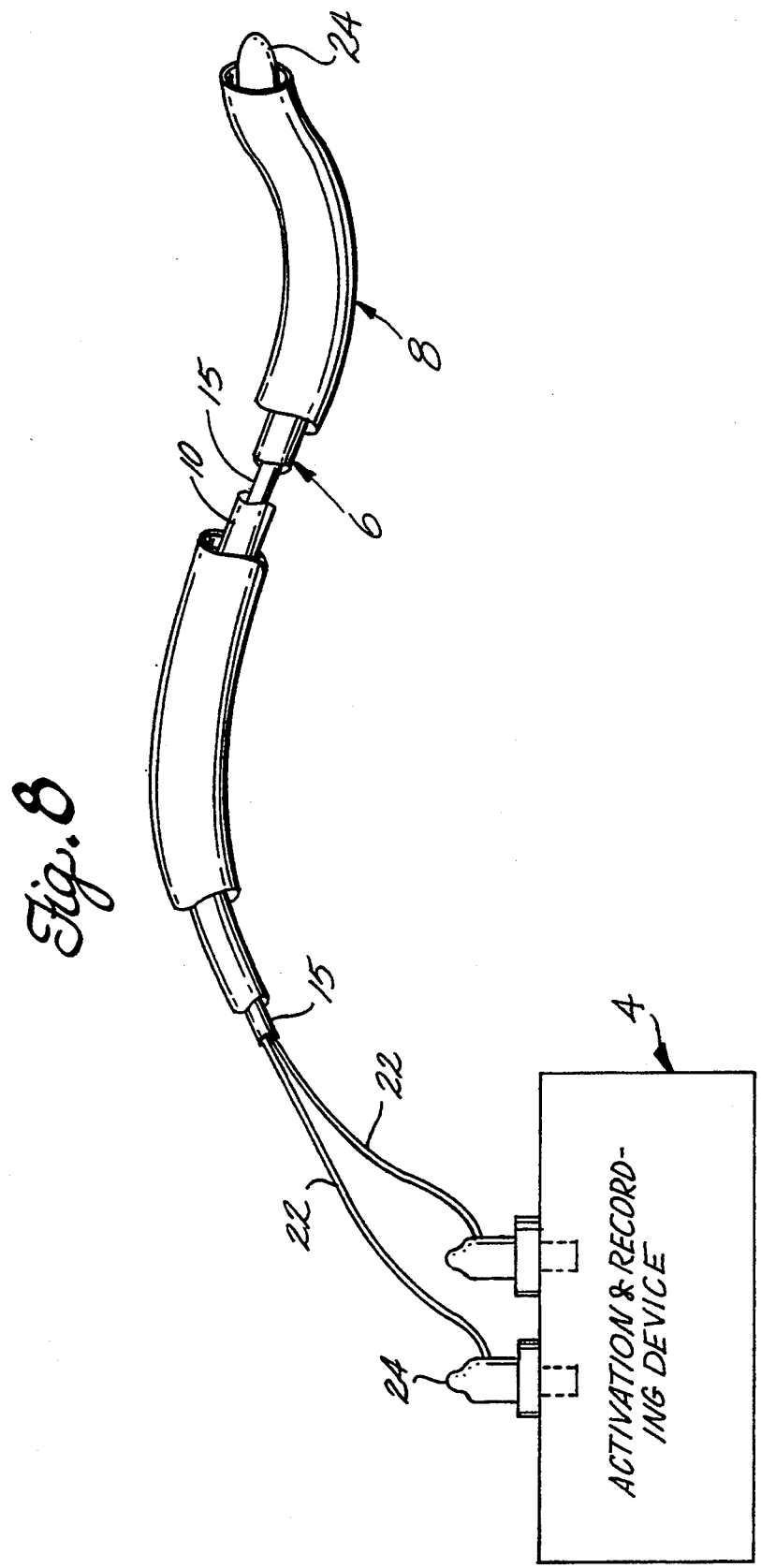

CARDIOVASCULAR CATHETER WITH LATERALLY STABLE BASKET-SHAPED ELECTRODE ARRAY

FIELD OF THE INVENTION

The present invention relates to cardiovascular catheters and, in particular, to such catheters having a retractable basket-shaped electrode array formed by a plurality of arms, each arm supporting a plurality of spaced-apart electrodes.

BACKGROUND OF THE INVENTION

Electrophysiology is a specialty within the field of cardiology for diagnosis and treatment of electrical abnormalities of the heart. Diagnosis is performed using electrode-bearing catheters placed within the heart chambers. Electrodes are positioned along a catheter shaft in a primarily two-dimensional array, although electrode elements spaced laterally around the catheter shaft give the array a very limited third dimension. Understandably, this third dimension is limited because of the small catheter shaft diameter required for such catheters as they are introduced into the heart via the veins and arteries of the body.

Electrical abnormalities are typically diagnosed by detecting the course of electrical activation paths along the endocardial surfaces of the heart chambers over time. To do this, the cardiologist may place several catheters within one or more chambers of the heart to get a better "picture" of this electrical activity. Sometimes this electrical activity is cyclical, i.e., repeats fairly well from heartbeat to heartbeat. In such cases, one catheter may serve to perform the diagnosis by moving the electrodes to various regions and then point-by-point comparing activation times with a reference. This reference may be the external EKG or another electrode catheter maintained in a stable position within a heart chamber.

However, certain types of electrical activity within a heart chamber are not cyclical. Examples include arterial flutter or arterial fibrillation, and ventricular tachycardia originating in scars in the wall of the ventricle that have resulted from infarcts. Such electrical activity is random from beat to beat. To analyze or "map" this type of electrical activity, the "picture" must be obtained during one beat. In other words, all the points of the map or picture must be obtained simultaneously within one-tenth of a second.

One solution to improve mapping is disclosed in U.S. Pat. Nos. 4,522,212 to Gelinas et al. and 4,699,147 to Chilson et al. In these patents, a catheter has, at its distal end, multiple lead-carrying arms which extend in a three-dimensional array, each arm having an inner central rib and electrodes spaced along its length. In Chilson et al., the arms are fixed at their distal end, but free to move within an outer catheter tube at their proximal end. The lead-carrying arms may be retracted into and extended from the outer catheter tube. The distal end of the catheter is directed to the designated areas of the heart and withdrawn, with the lead-carrying arms retracted within the outer catheter tube. Once at the designated areas, the arms are extended from the outer catheter tube to form a three-dimensional shape, referred to as an "elliptical envelope."

The catheter described in Chilson et al. is able to hold a large number of electrodes in different relative positions within a heart chamber. By this means, the cardiologist can obtain a map of electrical activity in one heartbeat by recording electrical signals from all the electrodes simultaneously. This is done by analyzing the spatial and temporal relationship of the electrical signals received at the electrodes.

By rotating the catheter and/or moving it longitudinally and recording electrical signals, a series of maps or pictures can be produced. A series of such pictures provides a "moving" picture of successive heartbeats, which may be able to better define the ectopic sites of activation or other activation pathways that contribute to the malfunction. This type of information may then allow the cardiologist to intervene with another catheter to destroy that causative tissue. Such destruction of heart tissue is referred to as "ablation," which is a rapidly growing field within electrophysiology and obviates the need for maximally invasive open heart surgery.

In Chilson et al. the arms are easily moved relative to each other and hence, the shape of the elliptical envelope varies from time to time and may vary even when positioned in one place due to the pumping heart chamber or the effect of rotation. Accordingly, the spatial relationship of the electrodes is subject to variation of unknown amounts. This, in turn, imparts a high degree of uncertainty or error in any map of electrical activity produced with the use of this catheter.

SUMMARY OF THE INVENTION

The present invention provides an electrophysiological mapping catheter comprising an outer catheter and an inner catheter. The inner catheter comprises a tubular shaft extending longitudinally through the outer catheter tube. At the distal end of the shaft, there is a plurality of flexible arms, each arm carrying a plurality of spaced-apart electrodes. The flexible arms of the basket are fixed at their proximal ends to a proximal fitting and fixed at their distal ends to a distal fitting. The shaft is movable longitudinally within the outer catheter and the arms and electrodes can be retracted into and extended from the outer catheter tube. When the arms are extended out of the catheter tube, the arms flex outwardly to form a "basket", the electrodes forming a three-dimensional array.

Each arm comprises a reinforcing spine surrounded by a tubular flexible sheath having a generally circular cross-section. Each reinforcing spine preferably has a semi-circular cross-section with the flat surface of the spine facing inwardly, i.e. toward the axis of the catheter. The spines preferably lie in the outwardly facing portion of the tubular sheath with the remainder of the tubular sheath filled by insulated electrode lead wires.

The electrodes are preferably formed on the arms by passing insulated lead wires through the wall of the tubular sheath, wrapping the wires around the tubular sheath and gluing it thereto. The insulation is then stripped off the outer surfaces of the lead wires which are wrapped around the sheath. The electrode lead wires extend from the arms through the proximal fitting and through the lumen of the inner catheter shaft to a stimulation and/or recording device.

The proximal and distal fittings include polygonal rod segments whose flat sides correspond in number to the number of spines and engage the flat surfaces of the spines. A clamping ring is positioned around the spines to hold them in proper orientation on the polygonal rod segment. In a preferred embodiment, the spines are formed out of a superelastic material, particularly a nickel-titanium alloy, with "shape memory." Such material returns to its bowed shape upon extension of the arms out of the outer catheter.

BRIEF DESCRIPTION OF THE DRAWINGS

FIG. 1 is an enlarged view of the distal end of an inner and an outer catheter with the inner catheter extended from the outer catheter, thus forming a basket of electrodes at the distal end of the inner catheter;

FIG. 2 is an enlarged view of an electrode pair from the circled portion labeled "2" in FIG. 1;

FIG. 3 is a longitudinal cross-sectional view of the distal end of the inner catheter shaft;

FIG. 8 is a partial perspective and partial schematic view of an electrophysiological mapping system according to the invention, including an inner catheter, an outer catheter, and an activation and recording device, showing the inner catheter retracted within the outer catheter.

DETAILED DESCRIPTION OF THE PREFERRED EMBODIMENT

Figure 4:
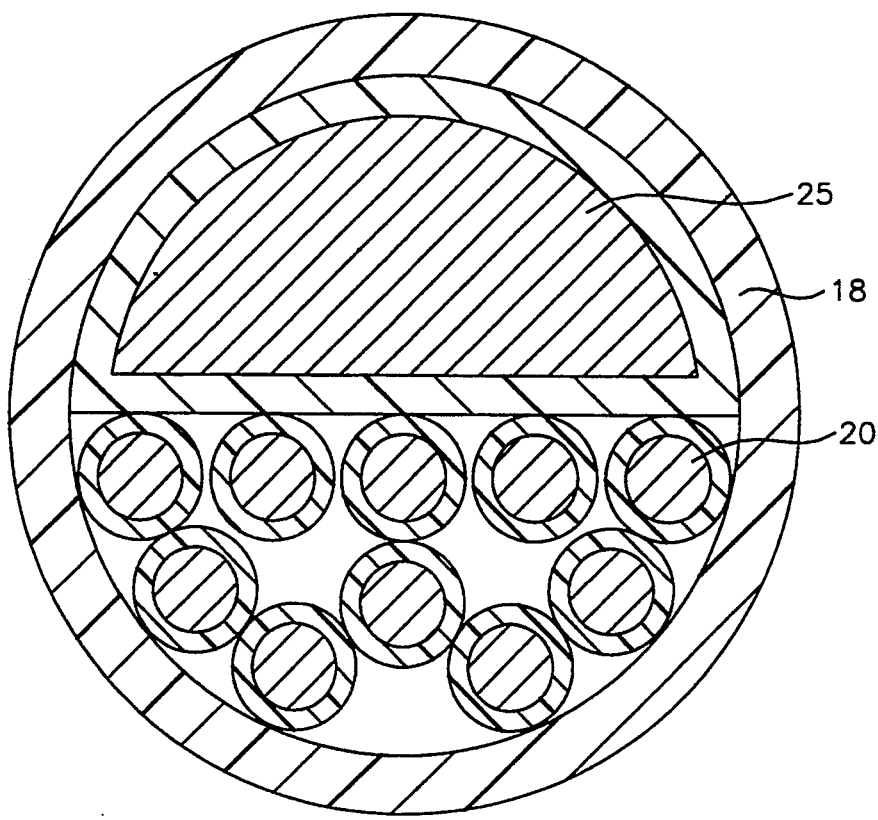
FIG. 4 is an enlarged transverse sectional view taken along line 4—4 of FIG. 1 and showing one arm of the basket of FIG. 1.
Figure 5:
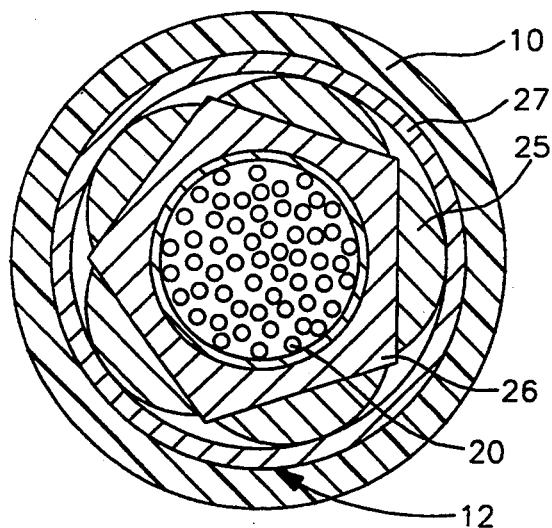
FIG. 5 is a transverse sectional view of a proximal fitting which has been taken along line 5—5 of FIG. 1.
Figure 6:
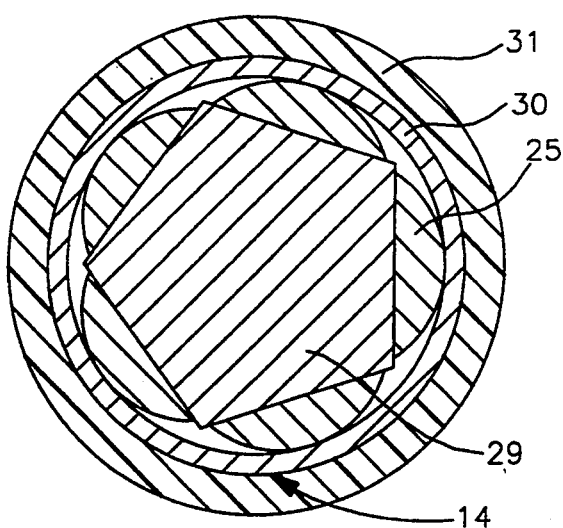
FIG. 6 is a transverse sectional view of a distal fitting of the basket of FIG. 1 taken along line 6—6 of FIG. 1.

With reference to FIGS. 1–7, a preferred electrophysiological mapping system is shown. The system includes an electronic stimulation and/or recording device, an inner catheter 6, and an outer catheter tube 8. Outer catheter tube 8 carries inner catheter 6 to a mapping site, e.g., within a heart chamber, and also serves to withdraw the inner catheter 6 from the mapping site. Inner catheter 6 is slidable longitudinally within outer catheter tube 8. A hemostasis valve, not shown, is provided at the proximal end of the outer catheter tube to prevent backflow of blood through the lumen of the outer catheter tube 8. FIG. 8 shows the mapping system, including electronic stimulation and/or recording device 4, and inner catheter 6 retracted within outer catheter tube 8.

Inner catheter 6 comprises an elongated, tubular catheter shaft 7 and five electrode carrying arms 9 at the distal end of the catheter shaft 7. Inner catheter 6 can be moved relative to outer catheter tube 8 between an extended position as shown in FIG. 1 wherein arms 9 extend completely out of the distal end of outer catheter tube 8 and a retracted position generally as shown in FIG. 8 wherein the arms 9 are retracted within the outer catheter tube 8. In the extended position, the arms 9 bow outwardly to define a "basket" structure.

Each arm 9 has its own spaced set of ten electrodes 11, shown herein as five hi-polar electrode pairs. In the embodiment shown, the five electrode pairs are generally evenly spaced. It is understood, however, that the number and spacing of the electrodes may vary as desired. Further, single electrodes may be used rather than bipolar electrode pairs.

The arms 9 are fixed at their proximal ends to a proximal fitting 12, and also fixed at their distal ends to a distal fitting 14. Proximal fitting 12 is, in turn, fixed to the distal end of the catheter shaft 7. The catheter shaft 7 comprises a central lumen 13 which extends from its proximal end to its distal end. The shaft 7 preferably comprises a tubular wall 10 of high-strength braided stainless steel or other high-strength wire or fiber, sandwiched between inner and outer layers of firm, yet flexible, polyurethane, for example, as disclosed in U.S. patent application Ser. No. 07/645,230, filed Jan. 24, 1991, incorporated by reference herein. This high-torque shaft structure allows a physician to control the orientation of the electrode basket within the heart chamber by rotating the catheter shaft 7 where it enters the patient's body, which is usually at the groin or neck. The shaft 7 preferably further comprises a nylon stiffening sleeve 15 lining the interior of the tubular wall 10.

FIG. 4 is a sectional view of an arm 9. The arm 9 has an outer tube 18 of a flexible insulating material, e.g., a plastic such as flexible polyurethane tubing. Inside the plastic tubing are the plurality of electrode lead wires 20, each wire having an insulation coating and a central conductive wire core. The wires 20 extend from the electrodes 11 through the plastic tubing 18 of the arms 9, through the proximal fitting 12 and lumen of the shaft 7 to the stimulation and/or recording device 4. In this embodiment, there are fifty lead wires 20 which correspond to the ten electrodes 11 carried on each of the five arms 9. The number of electrodes and, hence, electrode lead wires may be varied as needed.

The lead wires 20 are separated into five bundles 22, each bundle 22 containing the ten lead wires 20 which correspond to the ten electrodes 11 carried by each particular arm 9. At their proximal ends, the separate wire bundles 22 terminate in separate plug connectors 24, which are plugged into the activation and recording device 4. The total number of lead wires 20 in each bundle 22 is equal to the number electrodes 11 on each corresponding arm. Therefore, if there are 5 electrodes on each arm, there will be 5 leads in the corresponding bundle. If there are 5 electrode pairs, there will be 10 electrode leads in the bundle. Each bundle 22 of leads is contained in an insulated flexible tube, which in turn enters the plug connector.

With reference to FIG. 2, each electrode 11 is formed by passing a lead wire 20 through the outer tube 18 of the arm 9. The wire 20 is wrapped tightly around the tubing 18 and glued and then the insulation coating from the outwardly facing surfaces of the lead wires, i.e. the surfaces which will contact the heart wall, is stripped to expose the metal of the lead wire.

It is preferable that the electrode lead wires 20 be of a metal which is inert in blood. MONEL 400, which is a trademark of Huntington Alloy Products Division of International Nickel Co., Inc., Huntington, W. Va., is presently preferred. MONEL refers to a group of corrosion-resistant alloys of predominantly nickel and copper and very small percentages of carbon, manganese, iron, sulfur, and silicon. Some such alloys also contain a small percentage of aluminum, titanium, and cobalt. MONEL 400 has the additional benefit that it is not as easily visible under fluoroscopic x-ray as platinum. Therefore, the electrodes can be small and all of equal size and uniformly arranged.

With materials which are more radiopique, even spacing of the electrodes is not desirable because it is difficult to distringuish which arm is at which location. For example, in U.S. Pat. No. 4,699,147 to Chilson et al., the electrodes on one arm are spaced unevenly with respect to the electrodes on each other arm. If the electrodes were spaced evenly in the device of Chilson et al., it would be difficult to identify which arm is which under x-ray. In the preferred embodiment of the present invention, the electrode pairs on each arm are able to be spaced evenly with respect to each other and are located on corresponding positions to the electrodes on each other arm, although uneven spacing on each arm and staggered spacing with respect to the electrodes on other arms is acceptable.

The even spacing of electrodes would normally result in difficulty determining which arm is at which location. However, in accordance with one aspect of the invention, markers 38, at different locations along each arm, such as in a staggered or spiral pattern, are positioned on the arms, respectively. These markers preferably are of a material which is easily identifiable under fluoroscopic x-ray, such as platinum, and are in the shape of a band or ring fixed around each arm.

The arms 9 are supported by a flexible rib or spine 25 having a semi-circular cross-section. The spine 25 is preferably formed out of a superelastic material, such as a nickel-titanium alloy having about 54 to 57% nickel, preferably 55%, and the remainder is titanium, preferably 45%. Such materials exhibit superelasticity. That is, it can be deformed by an external stress, e.g. bent, and, when that stress is removed, it will return to its original shape. A presently preferred material is sold under the trademark NITINOL by U.S. Nitinol of Saratoga, Calif. Such a superelastic spine 25 allows the arms 9 of the basket to be retracted into and extended from the outer catheter tube 8 and otherwise subjected to bending, such as from the beating heart chamber, yet still return to its proper shape, even if extremely deformed.

The spine 25 preferably has an insulation coating, e.g., of polyurethane paint, to help hold it in place and shield it from the lead wires. The lead wires 20 and spine 25 are positioned in tube 18 such that the spine 25 occupies the outwardly facing portion of the tube 18, while the lead wires 20 occupy the inwardly facing portion of the tube 18. The terms "outwardly" and "inwardly" are relative to an axis or centerline of the basket. Spines 25 having a semi-circular cross-section are preferred over spines having circular cross-sections of the same cross-sectional area because they provide greater lateral stability, yet have sufficient flexibility for opening into the "basket" shape when the inner catheter 6 is extended out of and collapsed into outer catheter tube 8.

The positioning of the electrode lead wires 20 in the inward portion of the tube 18 places the wires 20 away from the heart wall. This enables the wire portion used for the electrodes 11 to pass through the tube 18 at a location remote from the heart wall and thereby provide a smoother electrode surface. The hole in the tube 18 through which the lead wire 20 extends and lead wire terminus is preferably covered and secured with an adhesive, e.g., polyurethane, in a position where it will not be in contact with the heart chamber wall.

The metal portion of each spine 25 extends beyond the plastic tubing 18 at each end and attaches to the two fittings 12 and 14, as shown in detail in FIGS. 3–6. The proximal fitting 12 is formed by a polygonal rod segment 26 having an axial aperture formed therein. The rod segment 26 is preferably metal. The number of sides of the polygonal rod segment 26 equal the number of spines 25. The flat surface of each spine 25 is positioned flat against the side of the polygonal rod segment 26 in the same orientation as the spines 25 are located in forming the basket.

An outer clamping ring 27, e.g., of metal, holds the spines 25 in place against the sides of the polygonal rod segment 26. An adhesive, such as polyurethane or epoxy, is preferably used to permanently fix the spines, polygonal rod segment 26 and clamping ring.

The proximal fitting 12 is fixedly mounted within the distal end of the inner catheter shaft 7, e.g., by epoxy, polyurethane or other adhesives. The distal end of the nylon sleeve 15 extends up to and butts against the proximal end of the polygonal rod segment 26 and clamping ring 27. The electrode lead wires 20 from each arm 9 pass through the axial aperture in the polygonal rod segment 26 and then through the nylon sleeve 15.

Distal fitting 14 is generally the same as proximal fitting 12, in that it has a polygonal rod segment 29. The spines 25 are fixed to each side, respectively, of the polygonal rod segment 29 and are secured thereto by an outer clamping ring 30. However, no aperture is needed in segment 29 because no lead wires are present at the distal fitting. In addition, it is preferable to provide an outer plastic tip member 31, which is rounded in shape at its distal end, to help the inner catheter slide through arteries or veins with minimum trauma and to prevent trauma in the heart chamber. The tip member 31 may be fixed by using adhesive, e.g., epoxy or polyurethane.

The distal fitting 14 is the same size as or, if desired, may be of a smaller scale than proximal fitting 12. These fittings 12 and 14 hold the spines 25 in proper angular orientation with respect to each other, and thus maintain the proper spacing of the arms 9 and the proper orientation of the basket. This is important because the cardiovascular catheter is subjected to a pumping heart wall and must also be rotated during the electrophysiological mapping process. In addition, the spines 25 are subjected to bending and other forces during retraction into the outer catheter and extension therefrom.

Figure 7:
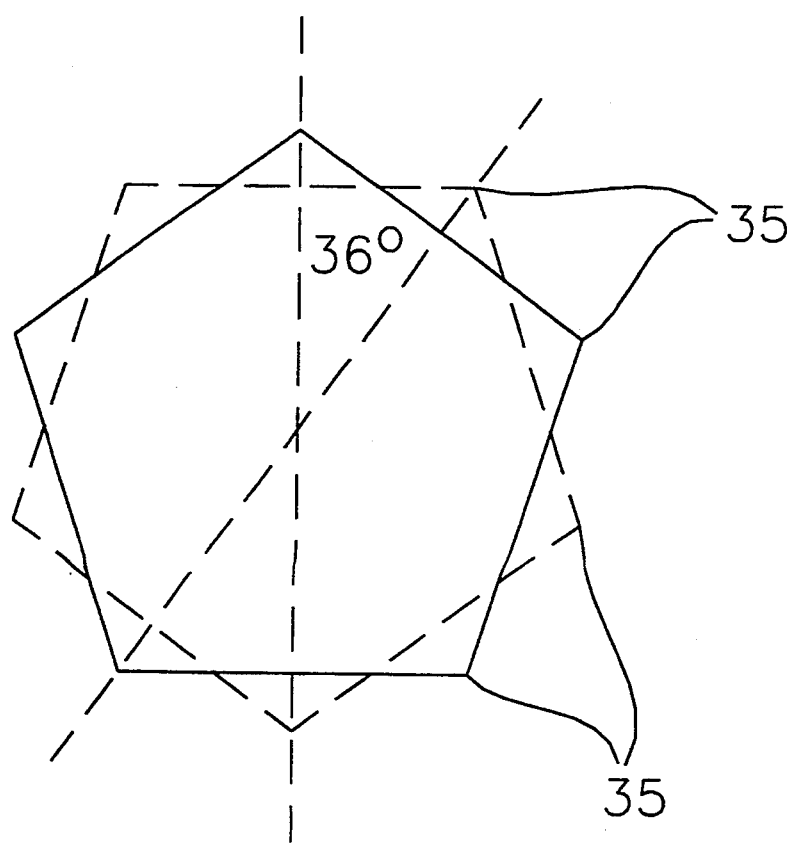
FIG. 7 is a schematic view of the ten assymetric positions of rotation.

The basket is shown with five arms 9, which is the most preferable number. As shown in FIG. 7, there are ten asymmetrical positions of rotation. That is, the arms are arranged so as to define the five corners of a pentagon, each corner corresponding to a position of rotation. Rotation of the basket by 36° provides five additional positions of rotation. By the use of five arms, the basket very nearly appears round in rotation when viewed axially. This feature greatly facilitates placement and control within a heart chamber because the heart chambers are not round, but are irregular.

A greater number of arms is not preferred because differentiation of electrodes becomes more difficult and the inner catheter is more difficult to fit within the outer catheter. A lesser number of arms is more practical in that it is smaller and easier to differentiate the electrodes, but is not preferred because mapping becomes more cumbersome.

In use, the inner catheter 6 is disposed within the outer catheter 8 for placement in a vein or artery and then subsequently into a chamber of the heart. The outer catheter 8 holds the arms 9 of the basket internally in a collapsed position so that the entire catheter, consisting of the inner catheter 6 and the outer or guiding catheter 8, can be passed down the vein or artery into the heart chamber. Once the distal end of the catheters has reached the desired heart chamber in the appropriate position, the outer catheter 8 is withdrawn so that the arms 9 flex into their predetermined "basket" position. The electrodes 11 contact the walls of the heart chamber in this position. Additional outward movement of the arms and pressure against the heart wall can be gained by pushing forward on the inner catheter shaft 7 causing the basket to widen outwardly. When mapping has been completed, the outer catheter can be extended back over the basket to collapse the arms, and then ultimately be withdrawn with the arms therein.

The inner mapping or basket catheter, as described above, has several advantages. For example, fixing the spines of the basket at both their distal and proximal ends provides a very laterally stable basket. This stability is important to hold the catheter in stabile position within a beating heart chamber.

The fittings which hold the distal and proximal ends of the spines together, the flat sides of the spines mating with the flat sides of the polygon, ensure accurate arrangement of the arms in three dimensions.

The semi-circular cross-section of the spines increases the lateral stiffness in comparison with a round cross-section of equal area, thereby increasing the lateral stability of the basket.

The use of superelastic material, such as NITINOL, for the spine results in a basket that can be bent, collapsed, and twisted without appreciable permanent deformation. It is thus highly resilient.

The use of five basket arms in conjunction with a high-torque catheter shaft achieves a basket which can readily be controlled and oriented within the heart chamber.

The use of the semi-circular cross-section for the spine further allows the spines to fill the outwardly facing portion of the arm tubing, thus leaving the inwardly facing portion for the lead wires. Lead wires can thus extend through the tubing, and after being wrapped around the tubing can terminate at locations along the inwardly facing side of the arms away from the heart wall. Each exit hole and terminus can be covered and secured by adhesive. Only the outwardly facing portions of the lead wire which is wrapped around the tubing need be scraped bare to form the electrode.

The electrodes can thus be made quite small and are readily distinguished fluoroscopically from the platinum ring markers. The ring markers readily identify each arm of the basket, as they are arranged in a staggered or spiral form on the different arms.

The basket which is formed as described is not only laterally stiff, but is also quite resilient and can form itself readily to the contour of the heart chamber, by pushing the inner catheter forward after the basket has been exposed to the heart chamber through the withdrawal of the outer catheter. This helps ensure that all electrodes make good contact with the endocardial surface and provide strong electrical recording signals.

The invention has been described in its preferred embodiment. Numerous variations of the invention will be evident to those of ordinary skill in the art. The appended claims not only cover the preferred embodiment, but also such variations.

What is claimed is:

1. A catheter for cardiac mapping comprising:
   (a) an elongated outer catheter tube;
   (b) an elongated inner catheter disposed within the outer catheter tube, said inner catheter comprising:
      (i) a tubular catheter shaft having a proximal end and a distal end and a central lumen;
      (ii) a plurality of flexible arms having distal and proximal ends said arms being connected at their proximal ends to the distal end of the catheter shaft, each arm carrying at least one electrode and wherein each arm comprises a reinforcing spine, an electrode lead wire electrically connected to each electrode carried on the arm and a tubular sheath surrounding the reinforcing spine and lead wires;
      (iii) a proximal fitting rigidly fixing the proximal ends of the arms together, the proximal fitting being fixed to the distal end of the catheter shaft and comprising a central aperture through which the lead wires extend; and
      (iv) a distal fitting fixing the distal ends of the arms together,
   (c) wherein the inner catheter is movable longitudinally within the outer catheter tube between a retracted position wherein the arms are disposed within the outer catheter tube and an extended position wherein the arms extend out of the distal end of the outer catheter tube and wherein the arms, in the extended position, bow outwardly to form a predetermined basket shape.

2. The catheter of claim 1 wherein the lead wires comprise an insulated coating and the electrodes are formed by passing end segments of the lead wires through the sheath, winding the end segments around the sheath and then stripping the insulated coating off at least a portion of the lead wire end segment wound around the sheath.

3. The catheter of claim 1 wherein the proximal and distal fittings each comprise a polygonal segment having a cross section in the shape of a polygon, the number of sides of the polygonal segment corresponding to the number of arms, and wherein each of the reinforcing spines of the arms has a proximal end which comprises a flat surface which engages a side of the polygonal segment of the proximal fitting, and a distal end of the spine comprises a flat surface which engages a flat surface of the polygonal segment of the distal fitting, and wherein the proximal and distal fittings each further comprise means for securing the ends of the spines of the arms to the polygonal segment.

4. The catheter of claim 3 wherein the means for securing the spines to the polygonal segments comprises a retaining ring which fits tightly around the spines, thereby holding the spines against the sides of the polygonal segment.

5. The catheter of claim 1 wherein there are five arms.

6. The catheter of claim 1 wherein the predetermined basket shape has a central axis, and each of the spines has a semi-circular transverse cross section with a flat side, the flat side of the spines facing toward the central axis.

7. The catheter of claim 6 wherein each spine of an arm is disposed in a portion of the sheath of that arm remote from the central axis of the basket and the electrode lead wires of that arm are disposed in the portion of the sheath of that arm nearer the central axis.

8. The catheter of claim 1 wherein the spines are made of NITINOL.

9. A catheter for cardiac mapping comprising:
   (a) an elongated outer catheter tube;
   (b) an elongated inner catheter disposed in the outer catheter tube and afforded longitudinal movement therein between retracted and extended positions, said inner catheter comprising:
      (i) a catheter body having a proximal end and a distal end;

(ii) a plurality of flexible arms extending from the distal end of the catheter body, each arm having a distal end and a proximal end; and (iii) means for fixing the distal ends of the arms together, (iv) wherein the arms bow outwardly between their proximal and distal ends and form a three-dimensional, predetermined shape with a central axis, the arms each comprising a tubular sheath, a plurality of electrode lead wires and a reinforcing spine extending within the sheath, and a plurality of electrodes electrically connected to the electrode lead wires at distal ends of the lead wires, the electrodes being disposed along the length of the sheath, said reinforcing spine comprising a semi-circular transverse cross-sectional shape having a flat side, with the flat side facing toward the central axis.

10. The catheter of claim 9 wherein the spines are made of NITINOL.

11. The catheter of claim 9 wherein the lead wires have an insulation coating and the electrodes are unitarily formed with the lead wires by passing the distal ends of the lead wires through the sheath, winding the distal ends around the sheath, and then stripping the insulation coating off at least a portion of the lead wire distal ends which are wound around the sheath.

12. The catheter of claim 9 wherein each arm has a marker disposed on the sheath at a predetermined position with respect to each other marker, each marker being staggered with respect to the predetermined position of each marker on each other sheath.

13. The catheter of claim 9 further comprising means for fixing the proximal ends of the arms together.

14. A catheter for cardiac mapping comprising:

(a) a catheter body having a proximal end and a distal end;

(b) a plurality of arms extending from the distal end of the catheter body, each arm having a distal end and a proximal end; and (c) means for fixing the distal ends of the arms together, wherein the arms bow outwardly between their proximal and distal ends and form a three-dimensional, predetermined shape with a central axis, each arm comprising a flexible tubular sheath, a plurality of electrode lead wires having an insulated coating and a reinforcing spine extending within the sheath, wherein an end portion of each electrode lead wire passes through the sheath at spaced intervals, is wound around the sheath and then stripped of its insulated coating to form a plurality of electrodes at spaced intervals along the length of the sheath, and wherein the electrode lead wires pass through the sheath at positions facing the central axis of the predetermined three-dimensional shape and are wound around the sheath such that a distal end of the end portion of each of the wires lies at a position facing the central axis.

15. The catheter of claim 14 further comprising a marker disposed along the length of each arm which is made of a material more prominent under x-ray than a material forming the electrodes, the marker on each arm being disposed in staggered relation with respect to each other marker.

16. The catheter of claim 15 wherein the markers comprise platinum, and the wires comprise MONEL.

17. An electrophysiological mapping device comprising:

an elongated tubular outer catheter having a distal end;

an elongated tubular inner catheter disposed within the outer catheter and slidable with respect thereto, the inner catheter having electrodes at a distal end thereof; and an electronic recorder electrically connected to the electrodes for electrically recording electric signals received by the electrodes, wherein the distal end of the inner catheter is extendable from and retractable into the distal end of the outer catheter, and wherein the inner catheter comprises:

(a) a tubular catheter body having a proximal end and a distal end;

(b) a plurality of flexible arms extending from the distal end of the catheter body, each arm having a distal end and a proximal end and comprising a flexible tubular sheath and a reinforcing spine having a semi-circular cross section extending within the sheath, each reinforcing spine having a proximal and a distal end, and wherein a plurality of electrodes are disposed along the length of the sheath;

(c) a first polygonal fitting fixing the proximal ends of the reinforcing spines together, the first fitting being fixed to the distal end of the catheter body; and (d) a second fitting fixing the distal ends of the reinforcing spines together, wherein, when the distal end of the inner catheter is extended from the distal end of the outer catheter, the arms bow outwardly and form a three-dimensional, predetermined basket shape; and wherein the electrodes are electrically connected to the recorder by insulated lead wires which extend from the recorder through the inner catheter body and sheaths of the arms to the electrodes.

18. The mapping device of claim 17 wherein each electrode is formed by an end segment of a lead wire which is passed through and wound around the sheath of an arm and then a portion of the wound segment is stripped of its insulation.

19. The mapping device of claim 17 wherein the first and second fittings each comprise a fitting member having a cross section in the shape of a polygon, the number of sides of the polygon corresponding to the number of spines, and wherein the proximal ends of the spines engage separate sides of the fitting member of the first fitting and the distal ends of the spines engage separate sides of the fitting member of the second fitting, and the first and second fitting member each further comprising means for securing the spines to the fitting member.

20. The mapping device of claim 17 wherein each arm has a marker disposed thereon which is made of a material more prominent under x-ray a material forming electrodes, the marker on each arm being disposed in staggered relation with respect to each other marker.

21. The catheter of claim 20 wherein the spines comprise NITINOL.

* * * * *

UNITED STATES PATENT AND TRADEMARK OFFICE
CERTIFICATE OF CORRECTION

PATENT NO. : 5,411,025
DATED : May 2, 1995
INVENTOR(S) : Wilton W. Webster, Jr.

It is certified that error appears in the above-indentified patent and that said Letters Patent is hereby corrected as shown below:

```
Column 3, line 8, after "inner" insert -- catheter --.
Column 3, line 22, change "assymetric" to
                -- asymetric --.
Column 3, line 59, change "hi-polar" to -- bi-polar --.
Column 4, line 64, change "distringuish" to
                -- distinguish --.
Column 5, line 6, after "each" delete "other".
Column 7, line 11, change "stabile" to -- stable --.
Column 10, line 60, after "x-ray" insert -- than --.
```

Signed and Sealed this

Third Day of October, 1995

Attest:

BRUCE LEHMAN

*Attesting Officer*   *Commissioner of Patents and Trademarks*